(12) United States Patent
Lim et al.

(10) Patent No.: US 6,835,213 B2
(45) Date of Patent: Dec. 28, 2004

(54) COMPOUNDS FOR HAIR COLORING COMPOSITIONS

(75) Inventors: Mu-Ill Lim, Cincinnati, OH (US); Margaret Popp, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 247 days.

(21) Appl. No.: 10/278,275

(22) Filed: Oct. 23, 2002

(65) Prior Publication Data

US 2004/0078904 A1 Apr. 29, 2004

(51) Int. Cl.$^7$ ................................................. A61K 7/13
(52) U.S. Cl. ........................ 8/405; 8/406; 8/408; 8/409; 8/410; 8/411; 8/421; 8/424; 564/355
(58) Field of Search .......................... 8/405, 406, 409, 8/410, 411, 421, 424; 564/355

(56) References Cited

U.S. PATENT DOCUMENTS

| | | | |
|---|---|---|---|
| 4,066,830 A | 1/1978 | Kormany et al. | 840/486 |
| 5,865,856 A | 2/1999 | Keller et al. | 8/410 |
| 6,010,541 A | 1/2000 | de la Mettrie | 8/412 |
| 6,027,538 A | 2/2000 | Vandenbossche | 8/409 |

FOREIGN PATENT DOCUMENTS

| | | | | |
|---|---|---|---|---|
| EP | 0399746 A | 11/1990 | | |
| EP | 1093793 A | 4/2001 | | |
| WO | WO 91/09885 | * 7/1991 | ............. | C08F/8/30 |
| WO | WO-98/27941 A1 | 7/1998 | | |
| WO | WO-98/52523 A1 | 11/1998 | | |
| WO | WO-01/62221 A1 | 8/2001 | | |

* cited by examiner

*Primary Examiner*—Yogendra N. Gupta
*Assistant Examiner*—Eisa Elhilo
(74) *Attorney, Agent, or Firm*—Marianne Dressman; Brian M. Bolam; Tara M. Rosnell

(57) ABSTRACT

Hair-coloring compositions comprise at least one self-coupling compound of Formula (1)

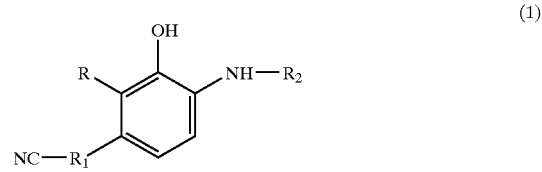

wherein R is a moiety selected from H, $C_{1-3}$ alkyl and $C_{1-3}$ hydroxyalkyl; $R_1$ is a $C_{1-3}$ alkylene radical and $R_2$ is selected from H and $C_{1-3}$ alkyl radicals.

19 Claims, No Drawings

COMPOUNDS FOR HAIR COLORING COMPOSITIONS

FIELD OF THE INVENTION

This invention relates to novel compounds and compositions for use in oxidative hair coloring comprising novel (4-amino or substituted amino-3-hydroxy-phenyl)-alkylnitrile compounds alone as self-coupling intermediates or couplers or with other couplers and with additional primary intermediates in combination with one or more oxidizing agents. The invention also relates to use of these hair coloring compositions for the coloration or dyeing of hair.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

In order to provide a full palette of shades, a source of yellow coloring is needed.

In permanent hair coloring, yellow coloration is generally obtained by the use of o-aminophenol or 5-methyl-2-aminophenol that gives a range of different yellow colorations with various couplers as well as through self-coupling. However, the resulting yellow colorations have poor wearability and stability to light, and some objections to their use has arisen from a toxicological standpoint. Additionally, only slight coloration intensity is achieved with o-aminophenol.

Sometimes yellow direct dye additives are used in oxidative hair color products as a source of yellow hair color. However, the drawback of utilizing such a coloration process for dyeing of hair is the relative fast and large loss of the yellow coloration experienced after repeated shampooing. Again, the consumer will notice undesirable color changes and loss of vibrancy.

It would therefore be desirable if a hair coloring system and composition for dyeing of hair could be provided that produces a yellow coloration of the hair that is more intense, exhibits wash fastness, and retains its intensity, brightness and vibrancy over a period of time, instead of showing a gradual loss and drabbing of the color.

BRIEF SUMMARY OF THE INVENTION

This invention provides dyeing compositions comprising one or more (4-amino or substituted amino-3-hydroxy-phenyl)-alkylnitrile compounds of the Formula (1) alone as a self-coupling intermediate or other couplers and additional primary intermediates in combination with one or more oxidizing agents.

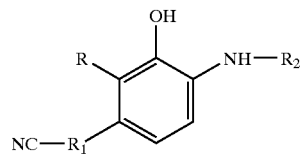

(1)

wherein R is a moiety selected from H, $C_{1-3}$ alkyl and $C_{1-3}$ hydroxyalkyl; $R_1$ is a $C_{1-3}$ alkylene radical and $R_2$ is selected from H and $C_{1-3}$ alkyl radicals.

These (4-amino or substituted amino-3-hydroxy-phenyl)-alkylnitrile compounds of the Formula (1) are self-coupling or may be coupled with one or more other couplers and also be combined with other couplers and primary intermediates for coloring hair.

These novel hair coloring compositions are used to provide coloration to hair in which there is good dye uptake by the hair and provides shades or colors which are stable over a relatively long period of time. The novel compositions provide for dyeing of hair to impart color or shades, especially yellow, possessing good wash fastness and wearability, good selectivity, and do not undergo significant change on exposure to light, shampooing or acid perspiration.

DETAILED DESCRIPTION OF THE INVENTION

The compounds of this invention are those of Formula (1)

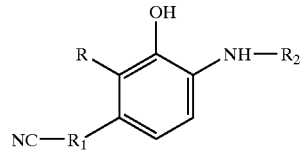

(1)

wherein R is a moiety selected from H, $C_{1-3}$ alkyl and $C_{1-3}$ hydroxyalkyl, preferably H; $R_1$ is a $C_{1-3}$ alkylene radical, preferably ethylene, and $R_2$ is selected from H and $C_{1-3}$ alkyl radicals.

The (4-amino or substituted amino-3-hydroxy-phenyl)-alkylnitriles of Formula (1) of this invention, where $R_2$ is H, may be prepared according to the following reaction sequence.

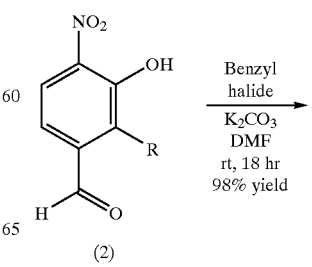

(2)

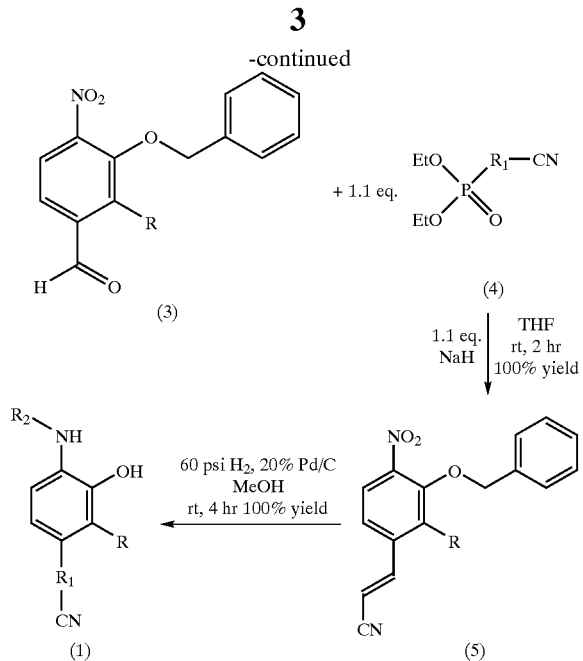

In this synthesis the new (4-amino or substituted amino-3-hydroxyphenyl)-alkylnitriles of Formula (1), of this invention, where $R_2$ is H, can be prepared by reaction of a 3-hydroxy-4-nitrobenzaldehyde of Formula (2) with a benzyl halide, such as benzyl bromide, in the presence of an inorganic base such as potassium carbonate in dimethylformamide (DMF) at room temperature for about 18 hours to produce the 3-benzyloxy-4-nitro-benzaldehyde compound of Formula (3) in about 98% yield; then reacting the compound of Formula (3) with diethyl cyanoalkylphosphonate of Formula (4) in a suspension of sodium hydride in anhydrous THF at room temperature for about 2 hours to produce 3-(3-benzyloxy-4-nitro-phenyl)-acrylonitrile of Formula (5) in about 100% yield; catalytically hydrogenating the compound of Formula (5) with 10% Pd on carbon at about 60 psi hydrogen at room temperature for about 4 hours to provide a compound of Formula (1) where $R_2$ is H in about 100% yield.

The compounds of Formula (1) wherein $R_2$ is $C_{1-3}$ alkyl are readily prepared by reaction of a compound of Formula (1) wherein $R_2$ is H with an appropriate aldehyde ($CH_2O$ or $R_3CHO$ where $R_3$ is $C_{2-3}$ alkyl) in the presence of a suitable reducing agent, such as for example, sodium borohydride, sodium cyanoborohydride or triacetoxyborohydride.

Using the above-described synthesis procedure 3-(4-amino-3-hydroxy-phenyl)-propionitrile was prepared in the following manner.

SYNTHESIS EXAMPLE 1

Synthesis of 3-(4-amino-3-hydroxy-phenyl)-propionitrile

3-Hydroxy-4-nitrobenzaldehyde (2) (4.18 g, 25 mmol) was dissolved in anhydrous DMF (100 mL). To this solution was added benzyl bromide (3.27 mL, 27.5 mmol) and potassium carbonate (3.8 g, 27.5 mmol). The reaction mixture was stirred at room temperature for 18 h, filtered and evaporated. The residue was taken up into ethyl acetate (250 mL) and water (250 mL). The organic layer was washed with brine (50 mL), dried over $MgSO_4$, filtered and evaporated leaving 3-benzyloxy-4-nitro-benzaldehyde (3) as an orange solid (6.31 g, 98% yield): $^1$HNMR (400 MHz, DMSO-$d_6$) δ 10.05 (s, 1H), 8.08 (d, J=8.0 Hz, 1H), 7.91 (s, 1H), 7.67 (d, J=8.0 Hz, 1H), 7.45 (m, 5H), 5.40 (s, 2H); $^{13}$CNMR (400 MHz, DMSO-$d_6$) δ 192.4, 151.2, 143.5, 139.9, 135.9, 128.9, 128.6, 127.9, 125.9, 122.7, 115.5, 71.1. To a suspension of sodium hydride (0.29 g, 12 mmol) in anhydrous THF (25 mL) at 0° C. was added via dropping funnel diethyl cyanomethylphosphonate (4) (1.94 mL, 12 mmol) in anhydrous THF (5 mL) followed by 3-benzyloxy-4-nitro-benzaldehyde (3) (2.6 g, 10 mmol) in anhydrous THF (30 mL). The reaction mixture was warmed up to room temperature and stirred for 2 h. The solvent was evaporated and the residue was taken up into ethyl acetate (50 mL) and water (25 mL). The organic phase was washed with brine (25 mL), dried over $MgSO_4$, filtered and evaporated leaving 3-(3-benzyloxy-4-nitro-phenyl)-acrylonitrile (5) as an orange-red solid (0.28 g, 100% yield): $^1$HNMR (400 MHz, DMSO-$d_6$) δ 8.04 (d, J=8.0 Hz, 1H), 7.77 (s, 1H), 7.71 (d, J=16.6 Hz, 1H), 7.45 (m, 6H), 6.72 (d, J=16.6 Hz, 1H), 5.33 (s, 2H); $^{13}$CNMR (400 MHz, DMSO-$d_6$) δ 151.4, 148.9, 140.8, 139.5, 136.0, 128.9, 128.6, 128.0, 126.0, 120.7, 118.5, 114.5, 101.3, 71.1; MS calculated for $C_{16}H_{12}N_2O_3$ $(M)^+$: 280. found 280. 3-(3-Benzyloxy-4-nitro-phenyl)-(5) (0.28 g, 1.0 mmol) was dissolved in anhydrous methanol (20 mL). To this solution was added 10% palladium on carbon (56 mg, 20% wt) under a blanket of carbon dioxide. The hydrogenation was carried out under 60 psi of hydrogen at room temperature for 4 h, filtered through a pad of Celite and evaporated to yield an orange oil. This oil was stirred in hexane, decanted and vacuum dried leaving 3-(4-amino-3-hydroxy-phenyl)-propionitrile (1) as an orange solid (0.58 g, 100% yield): $^1$HNMR (400 MHz, DMSO-$d_6$) δ 8.81 (bs, 1H), 6.31 (m, 3H), 4.30 (bs 2H), 3.18 (s, 2H), 2.35 (s, 2H); $^{13}$CNMR (400 MHz, DMSO-$d_6$) δ 144.3, 135.5, 127.1, 120.8, 119.6, 114.9, 30.5, 19.2; MS calculated for $C_9H_{10}N_2O$ $(M)^+$: 162. found 162.

As used herein, the term "hair dyeing composition" (also synonymously referred to herein as the hair dye composition, the hair coloring composition, or the hair dye lotion) refers to the composition containing oxidation dyes, including the compounds described herein, prior to admixture with the developer composition. The term "developer composition" (also referred to as the oxidizing agent composition or the peroxide composition) refers to compositions containing an oxidizing agent prior to admixture with the hair dyeing composition. The term "hair dye product" or "hair dye system" (also referred to as the hair dyeing system, hair dyeing product, or hair coloring system) interchangeably refer to the combination of the hair dyeing composition and the developer composition before admixture, and may further include a conditioner product and instructions, such product or system often being provided packaged as a kit. The term "hair dyeing product composition" refers to the composition formed by mixing the hair dyeing composition and the developer composition. "Carrier" (or vehicle or base) refers to the combination of ingredients contained in a composition excluding the active agents (e.g., the oxidation hair dyes of the hair dyeing composition). Unless otherwise indicated all percentages are by weight unless other unit basis are indicated.

For hair coloring compositions of this invention, there may be used one or more of the 3-(4-amino or substituted amino-3-hydroxy-phenyl)-alkylnitrile compounds alone or in combination with one or more other couplers. The hair coloring compositions of this invention can also include one or more other primary intermediate compounds, if so desired.

Suitable other primary intermediates include, for example:

p-phenylenediamine derivatives such as: benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl) benzene-1,4-diamine, 2-[(4-amino-phenyl)-(2-hydroxy-ethyl)-amino]-ethanol, (commonly known as N,N-bis(2-hydroxyethyl)-p-phenylenediamine)(2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy}ethoxy)ethoxy]benzene-1,4-diamine;

p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)-phenol, and 4-amino-2-fluoro-phenol;

o-aminophenol derivatives such as: 2-amino-phenol (commonly known as o-aminophenol), 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, and 1-(4-chlorobenzyl)-1H-pyrazole-4,5-diamine.

Suitable other couplers include, for example:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chlorobenzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, N-(2-aminoethyl)benzene-1,3-diamine, 4-{[(2,4-diamino-phenyl)oxy]methoxy}-benzene-1,3-diamine, and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino) ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane-1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine, 1-methyl-1H-pyrazole-4,5-diamine, 2-(4,5-diamino-1H-pyrazol-1-yl)ethanol, 1-(4-methylbenzyl)-1H-pyrazole-4,5-diamine, 1-(benzyl)-1H-pyrazole-4,5-diamine, and $N^2,N^2$-dimethyl-pyridine-2,5-diamine.

Preferred other couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine, 2-(4,5-diamino-1H-pyrazol-1-yl)ethanol, 1-(4-methylbenzyl)-1H-pyrazole-4,5-diamine, and 1-(benzyl)-1H-pyrazole-4,5-diamine.

Most preferred other couplers include:

phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

Understandably, the coupler compounds and the primary intermediate compounds, including the compounds (1) of this invention, in so far as they are bases, can be used as free bases or in the form of their physiologically compatible salts with organic or inorganic acids, such as hydrochloric, citric, acetic, tartaric, or sulfuric acids, or, in so far as they have aromatic OH groups, in the form of their salts with bases, such as alkali phenolates.

The total amount of dye precursors (e.g., primary intermediate and coupler compounds, including the compounds of this invention) in the hair dyeing compositions of this invention is generally from about 0.002 to about 20, preferably from about 0.04 to about 10, and most preferably from about 0.1 to about 7.0 weight percent, based on the total weight of the hair dyeing composition. The primary intermediate and coupler compounds are generally used in molar equivalent amounts. However, it is possible to use the primary intermediate compounds in either excess or deficiency, i.e., a molar ratio of primary intermediate to coupler generally ranging from about 5:1 to about 1:5.

The hair dyeing compositions of this invention will contain the Formula (1) compound(s) either alone or with other couplers and optionally with primary intermediates in an effective dyeing amount, each of compounds of Formula (1), the primary intermediate and coupler being generally in an amount of from about 0.001 to about 10 weight percent by weight of the hair dye composition, preferably from about 0.01 to about 5.0 weight percent. Other couplers, when present, are typically present in an amount such that in aggregate the concentration of couplers and the compounds of Formula (1) in the composition is from about 0.002 to about 10 weight percent, preferably from about 0.01 to about 5.0 weight percent. Other primary intermediates when present are present in an effective dyeing concentration, generally an amount of from about 0.001 to about 10.0 weight percent by weight of the hair dye composition, preferably from about 0.01 to about 5.0 weight percent. The remainder of the hair dye composition comprises a carrier or vehicle for the couplers and primary intermediates, and comprises various adjuvants as described below.

Any suitable carrier or vehicle, generally an aqueous or hydroalcoholic solution, can be employed, preferably an aqueous solution. The carrier or vehicle will generally comprise more than 80 weight percent of the hair dye composition, typically 90 to 99 weight percent, preferably 94 to 99 weight percent. The hair coloring compositions of this invention may contain as adjuvants one or more cationic, anionic, amphoteric, or zwitterionic surface active agents, perfumes, antioxidants such as ascorbic acid, thioglycolic acid or sodium sulfite, chelating and sequestering agents such as EDTA, thickening agents, alkalizing or acidifying agents, solvents, diluents, inerts, dispersing agents, penetrating agents, defoamers, enzymes, and other dye agents (e.g., synthetic direct and natural dyes). These adjuvants are cosmetic additive ingredients commonly used in compositions for coloring hair.

The hair dye compositions of the present invention are used by admixing them with a suitable oxidant, which reacts with the hair dye precursors to develop the hair dye. Any suitable oxidizing agent can be employed in the hair dye product compositions of this invention, particularly hydrogen peroxide ($H_2O_2$) or precursors therefor. Also suitable are urea peroxide, the alkali metal salts of persulfate, perborate, and percarbonate, especially the sodium salt, and melamine peroxide. The oxidant is usually provided in an aqueous composition generally referred to as the developer composition, which normally is provided as a separate component of the finished hair dye product and present in a separate container. The developer composition may also contain, to the extent compatible, various ingredients needed to form the developer composition, i.e., peroxide stabilizers, foam formers, etc., and may incorporate one or more of the adjuvants referred to above, e.g., surface active agents, thickeners, pH modifiers, etc. Upon mixing the hair coloring composition and the developer composition to form a hair dye product composition, the adjuvants are provided in the hair dye product composition as it is applied to the hair to achieve desired product attributes, e.g., pH, viscosity, rheology, etc.

The form of the hair dye product compositions according to the invention can be, for example, a solution, especially an aqueous or aqueous-alcoholic solution. However, the form that is preferred is a thick liquid, cream, gel or an emulsion whose composition is a mixture of the dye ingredients with the conventional cosmetic additive ingredients suitable for the particular preparation.

Suitable conventional cosmetic additive ingredients useful in the hair dye and developer compositions, and hence in the hair dye product compositions of this invention are described below, and may be used to obtain desired characteristics of the hair dye, developer and hair dye product compositions.

Solvents: In addition to water, solvents that can be used are lower alkanols (e.g., ethanol, propanol, isopropanol, benzyl alcohol); polyols (e.g., carbitols, propylene glycol, hexylene glycol, glycerin). See WO 98/27941 (section on diluents) incorporated by reference. See also U.S. Pat. No. 6,027,538 incorporated by reference. Under suitable processing, higher alcohols, such as C8 to C18 fatty alcohols, especially cetyl alcohol, are suitable organic solvents, provided they are first liquified by melting, typically at low temperature (50 to 80° C.), before incorporation of other, usually lipophilic, materials.

The organic solvents are typically present in the hair dye compositions in an amount of from about 5 to about 30% by weight of the hair dye composition. Water is usually present in an amount of from about 5 to about 90% by weight of the hair dye composition, preferably from about 15 to about 75% by weight and most preferably from about 30 to about 65% by weight.

Surfactants: These materials are from the classes of anionic, cationic, amphoteric (including zwitterionic surfactants) or nonionic surfactant compounds. (Cationic surfactants, generally included as hair conditioning materials, are considered separately below.) Suitable surfactants, other than cationic surfactants, include fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated fatty acids, ethoxylated alkylphenols, block polymers of ethylene and/or propylene glycol, glycerol esters, phosphate esters, fatty acid alkanol amides and ethoxylated fatty acid esters, alkyl sulfates, ethoxylated alkyl sulfates, alkyl glyceryl ether sulfonates, methyl acyl taurates, acyl isethionates, alkyl ethoxy carboxylates, fatty acid mono- and diethanolamides. Especially useful are sodium and ammonium alkyl sulfates, sodium and ammonium ether sulfates having 1 to 3 ethylene oxide groups, and nonionic surfactants sold as Tergitols, e.g., C11-C15 Pareth-9, and Neodols, e.g., C12-C15 Pareth-3. They are included for various reasons, e.g., to assist in thickening, for forming emulsions, to help in wetting hair during application of the hair dye product composition, etc. Amphoteric surfactants include, for example, the asparagine derivatives as well betaines, sultaines, glycinates and propionates having an alkyl or alkylamido group of from about 10 to about 20 carbon atoms. Typical amphoteric surfactants suitable for use in this invention include lauryl betaine, lauroamphoglycinate, lauroamphopropionate, lauryl sultaine, myristamidopropyl betaine, myristyl betaine, stearoamphopropylsulfonate, cocamidoethyl betaine, cocamidopropyl betaine, cocoamphoglycinate, cocoamphocarboxypropionate, cocoamphocarboxyglycinate, cocobetaine, and cocoamphopropionate. Reference is made to WO 98/52523 published Nov. 26, 1998 and WO 01/62221 published Aug. 30, 2001, both incorporated herein by reference thereto.

The amount of surfactants in the hair dye compositions is normally from about 0.1% to 30% by weight, preferably 1% to 15% by weight.

Thickeners: Suitable thickeners include such as higher fatty alcohols, starches, cellulose derivatives, petrolatum, paraffin oil, fatty acids and anionic and nonionic polymeric thickeners based on polyacrylic and polyurethane polymers. Examples are hydroxyethyl cellulose, hydroxymethylcellulose and other cellulose derivatives, hydrophobically modified anionic polymers and nonionic polymers, particularly such polymers having both hydrophilic and hydrophobic moieties (i.e., amphiphilic polymers). Useful nonionic polymers include polyurethane derivatives such as PEG-150/stearyl alcohol/SDMI copolymer. Suitable polyether urethanes are Aculyn® 22, 44 and Aculyn® 46 polymers sold by Rohm & Haas. Other useful amphiphilic polymers are disclosed in U.S. Pat. No. 6,010,541 incorporated by reference. See also WO 01/62221 mentioned above. Examples of anionic polymers that can be used as thickeners are acrylates copolymer, acrylates/ceteth-20 methacrylates copolymer, acrylates/ceteth-20 itaconate copolymer, and acrylates/beheneth-25 acrylates copolymers. In the case of the associative type of thickeners, e.g., Aculyns 22, 44 and 46, the polymer may be included in one of either the hair dye composition or the developer composition of the hair dye product and the surfactant material in the another. Thus, upon mixing of the hair dye and developer compositions, the requisite viscosity is obtained. The thickeners are provided in an amount to provide a suitably thick product as it is applied to the hair. Such products generally have a viscosity of from 1000 to 100000 cps, and often have a thixotropic rheology.

pH Modifying agents: Suitable materials that are used to adjust pH of the hair dye compositions include alkalizers such alkali metal and ammonium hydroxides and carbonates, especially sodium hydroxide and ammonium carbonate, ammonia, organic amines including methylethanolamine, aminomethylpropanol, mono-, di-, and triethanolamine, and acidulents such as inorganic and inorganic acids, for example phosphoric acid, acetic acid, ascorbic acid, citric acid or tartaric acid, hydrochloric acid, etc. See U.S. Pat. No. 6,027,538 incorporated by reference.

Conditioners: Suitable materials include silicones and silicone derivatives; hydrocarbon oils; monomeric quaternary compounds, and quaternized polymers. Monomeric quaternary compounds are typically cationic compounds, but may also include betaines and other amphoteric and zwitterionic materials that provide a conditioning effect. Suitable monomeric quaternary compounds include behentrialkonium chloride, behentrimonium chloride, benzalkonium bromide or chloride, benzyl triethyl ammonium chloride, bis-hydroxyethyl tallowmonium chloride, C12-18 dialkyldimonium chloride, cetalkonium chloride, ceteartrimonium bromide and chloride, cetrimonium bromide, chloride and methosulfate, cetylpyridonium chloride, cocamidoproypl ethyidimonium ethosulfate, cocamidopropyl ethosulfate, coco-ethyldimonium ethosulfate, cocotrimonium chloride and ethosulfate, dibehenyl dimonium chloride, dicetyldimonium chloride, dicocodimonium chloride, dilauryl dimonium chloride, disoydimonium chloride, ditallowdimonium chloride, hydrogenated tallow trimonium chloride, hydroxyethyl cetyl dimonium chloride, myristalkonium chloride, olealkonium chloride, soyethomonium ethosulfate, soytrimonium chloride, stearalkonium chloride, and many other compounds. See WO 98/27941 incorporated by reference. Quaternized polymers are typically cationic polymers, but may also include amphoteric and zwitterionic polymers. Useful polymers are exemplified by polyquaternium-4, polyquaternium-6, polyquaternium-7, polyquaternium-8, polyquaternium-9, polyquaternium-10, polyquaternium-22, polyquaternium-32, polyquaternium-39, polyquaternium-44 and polyquaternium-47. Silicones suitable to condition hair are dimethicone, amodimethicone, dimethicone copolyol and dimethiconol. See also WO 99/34770 published Jul. 15, 1999, incorporated by reference, for suitable silicones. Suitable hydrocarbon oils would include mineral oil.

Conditioners are usually present in the hair dye composition in an amount of from about 0.01 to about 5% by weight of the composition.

Direct Dyes: The hair dyeing compositions according to the invention can also contain compatible direct dyes including Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, and Disperse Blue 377. These direct dyes can be contained in the hair coloring compositions of the invention in an amount of from about 0.05 to 4.0 percent by weight.

Natural ingredients: For example, proteins and protein derivatives, and plant materials such as aloe, chamomile and henna extracts.

Other adjuvants include polysaccharides, alkylpolyglycosides, buffers, chelating and sequestrant agents, antioxidants, and peroxide stabilizing agents as mentioned in WO 01/62221, etc.

The adjuvants referred to above but not specifically identified that are suitable are listed in the International Cosmetics Ingredient Dictionary and Handbook, (Eighth Edition) published by The Cosmetics, Toiletry, and Fragrance Association, incorporated by reference. In particular reference is made to Volume 2, Section 3 (Chemical Classes) and Section 4 (Functions) are useful in identifying a specific adjuvant to achieve a particular purpose or multipurpose.

The above-mentioned conventional cosmetic ingredients are used in amounts suitable for their functional purposes. For example, the surfactants used as wetting agents, associative agents, and emulsifiers are generally present in concentrations of from about 0.1 to 30 percent by weight, the thickeners are useful in an amount of from about 0.1 to 25 percent by weight, and the hair care functional materials are typically used in concentrations of from about 0.01 to 5.0 percent by weight.

The hair dyeing product composition as it is applied to the hair, i.e., after mixing the hair dye composition according to the invention and the developer, can be weakly acidic, neutral or alkaline according to their composition. The hair dye compositions can have pH values of from about 6 to 11.5, preferably from about 6.8 to about 10, and especially from about 8 to about 10. The pH of the developer composition is typically acidic, and generally the pH is from about 2.5 to about 6.5, usually about 3 to 5. The pH of the hair dye and developer compositions is adjusted using a pH modifier as mentioned above.

In order to use the hair coloring composition for dyeing hair, the above-described hair coloring compositions according to the invention are mixed with an oxidizing agent immediately prior to use and a sufficient amount of the mixture is applied to the hair, according to the hair abundance, generally from about 60 to 200 grams. Some of the adjuvants listed above (e.g., thickeners, conditioners, etc.) can be provided in the dye composition or the developer, or both, depending on the nature of the ingredients, possible interactions, etc., as is well known in the art.

Typically, hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. If a 6 percent hydrogen peroxide solution is used as oxidizing agent, the weight ratio of hair coloring composition to the developer composition is 5:1 to 1:5, but preferably 1:1. In general, the hair dyeing composition comprising primary intermediate(s) and coupler(s) is prepared and at the time of use is admixed with the developer composition containing the oxidizing agent to obtain an essentially homogenous, preferably thickened, composition (the hair dye product composition). Upon such preparation the hair dye product composition is applied to the hair to be dyed and remains in contact with the hair for an amount of time effective to dye the hair. The hair dye product composition is allowed to act on the hair for about 2 to about 60 minutes, preferably about 15 to 45, especially about 30 minutes, at about 15 to 50° C. Thereafter, the hair is rinsed with water, to remove the hair dye product composition and dried. If necessary, the hair is washed with a shampoo and rinsed, e.g., with water or a weakly acidic solution, such as a citric acid or tartaric acid solution, and dried. Optionally, a separate conditioning product may also be provided.

Together, the hair dye composition and the developer composition form a system for dyeing hair. This system may be provided as a kit comprising in a single package separate containers of the hair dye composition, the developer, the optional conditioner or other hair treatment product, and instructions for use.

Especially useful primary intermediate and coupler combinations of this invention will provide coloring compositions having outstanding color fastness, fastness to washing, fastness to rubbing, and good selectivity.

It has surprisingly been discovered that when a 3-(4-amino or substituted amino-3-hydroxy-phenyl)-alkylnitrile couples to color piedmont hair the hair is colored a more intense yellow color then when the hair is colored by coupling o-aminophenol. Additionally when a 3-(4-amino or substituted amino-3-hydroxy-phenyl)-alkylnitrile couples to color piedmont hair the hair is colored with a significantly better wash fastness than such hair colored with 5-methyl-2-aminophenol.

The advantageous properties of the hair-coloring compositions of this invention compared to closely related hair-coloring composition are illustrated by the following tests.

DYEING EXAMPLE 1

Piedmont hair weighing from 700 to 900 mg was used. The following composition shown in Table 1 was used for dyeing piedmont hair. The dyeing solution of 1 g was mixed with 1 g of 20 volume hydrogen peroxide. The resulting mixture was applied to the hair and permitted to remain in contact with hair for 30 minutes at room temperature. Thus dyed hair was then shampooed and rinsed with water and dried. Minolta spectrophotometer CM-3700d from Minolta Co. was used. Color space is CIE L*a*b* and illuminant is D65 daylight with 10° observer (Table 1, 2 and 3).

TABLE 1

| Composition | A (%) | B (%) | C (%) |
|---|---|---|---|
| Cocamidopropyl betaine | 17.00 | 17.00 | 17.00 |
| Ethanolamine | 2 | 2 | 2 |
| Oleic Acid | 0.75 | 0.75 | 0.75 |
| Citric Acid | 0.1 | 0.1 | 0.1 |
| Ammonium hydroxide | 5.0 | 5.0 | 5.0 |
| Behentrimonium chloride | 0.5 | 0.5 | 0.5 |
| Sodium sulfite | 0.1 | 0.1 | 0.1 |
| EDTA | 0.1 | 0.1 | 0.1 |
| Erythorbic acid | 0.4 | 0.4 | 0.4 |
| 2-Aminophenol | 1.09 | | |
| 2-Amino-5-methylphenol | | 1.23 | |
| 3-(4-amino-3-hydroxy-phenyl)-propionitrile | | | 1.62 |
| Water | QS 100 | QS 100 | QS 100 |
| Shade on piedmont hair | Yellow Orange | Yellow | Yellow |

TABLE 2

The CIE L*a*b* values obtained from Composition A, B and C

| Composition | L* | a* | b* |
|---|---|---|---|
| Piedmont Hair | 73.20 | 2.92 | 28.11 |
| Comp. A | 68.13 | −1.83 | 26.56 |
| Comp. B | 69.52 | −2.57 | 56.05 |
| Comp. C | 66.48 | −3.51 | 37.36 |

TABLE 3

Coupling of Compound of Invention with various couplers

| Composition | D (%) | E (%) | F (%) |
|---|---|---|---|
| Cocamidopropyl betaine | 17.00 | 17.00 | 17.00 |
| Ethanolamine | 2 | 2 | 2 |
| Oleic Acid | 0.75 | 0.75 | 0.75 |
| Citric Acid | 0.1 | 0.1 | 0.1 |
| Ammonium hydroxide | 5.0 | 5.0 | 5.0 |
| Behentrimonium chloride | 0.5 | 0.5 | 0.5 |
| Sodium sulfite | 0.1 | 0.1 | 0.1 |
| EDTA | 0.1 | 0.1 | 0.1 |
| Erythorbic acid | 0.4 | 0.4 | 0.4 |
| 3-(4-amino-3-hydroxy-phenyl)-propionitrile | 1.62 | 1.62 | 1.62 |
| 1-Naphthol | 1.44 | | |
| 2-Methyl-1-naphthol | | 1.58 | |
| 5-Amino-2-methylphenol | | | 1.23 |
| Water | QS 100 | QS 100 | QS 100 |

TABLE 3-continued

Coupling of Compound of Invention with various couplers

| Composition | D (%) | E (%) | F (%) |
|---|---|---|---|
| Shade on piedmont hair | Yellow | Orange yellow | Yellow orange |
| CIE L*a*b* | L* 70.07 | L* 60.29 | L* 61.35 |
|  | a* 1.33 | a* 12.41 | a* 6.39 |
|  | b* 29.41 | b* 23.32 | b* 22.91 |

Wash Fastness Test

Hair swaches dyed with 3-(4-amino-3-hydroxy-phenyl)-propionitrile and 5-methyl-2-aminophenol were placed in a container filled with 50 mL of 10% (wt) of Herbal Essences Shampoo™ in deionized water. The container was agitated for 3 h, rinsed, combed and dried. Color changes were measured by Minolta spectrophotometer CM-3700d from Minolta Co. (Table 4). Color space is CIE L*a*b* and illuminant is D65 daylight with 10° observer.

TABLE 4

WASH FASTNESS OF 3-(4-AMINO-3-HYDROXY-PHENYL)-PROPIONITRILE AND 5-METHYL-2-AMINOPHENOL

| | Before | | | After 3 h wash | | | |
|---|---|---|---|---|---|---|---|
| Compound | L* | a* | b* | L* | a* | b* | ΔE |
| 3-(4-amino-3-hydroxy-phenyl)-propionitrile | 61.91 | 3.74 | 44.97 | 64.88 | 0.68 | 38.52 | 7.73 |
| 5-methyl-2-aminophenol | 60.97 | 1.78 | 49.94 | 61.94 | −0.26 | 35.04 | 15.01 |

$\Delta E$ = square root of $(\Delta L^*)^2 + (\Delta a^*)^2 + (\Delta b^*)^2$

The total color change (ΔE 7.73) for 3-(4-amino-3-hydroxy-phenyl)-propionitrile is much smaller than that (ΔE 15.01) for 5-methyl-2-aminophenol.

Exemplary combinations of hair coloring components employing a novel compound of Formula (1) of this invention are shown in combinations C1 to C138 in Tables A through H. Reading down the columns in Tables A through H, the Xes designate the dye compounds (including the compounds of this invention and other primary intermediates and couplers) that form illustratively suitable combinations of dyes that can be formulated according to the present invention. For example, in Combination No. C1 in Column 4 of Table A, a compound of Formula (1) of this invention, wherein R, $R_1$, and $R_2$ are as defined hereinbefore, can be combined with 2-methyl-benzene-1,4-diamine and 2-aminophenol.

TABLE A

| | | Dye Combinations | | | | | | | | | | | |
|---|---|---|---|---|---|---|---|---|---|---|---|---|---|
| Structure | IUPAC Name | Name | C1 | C2 | C3 | C4 | C5 | C6 | C7 | C8 | C9 | C10 | C11 |
| 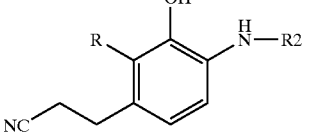 | | | X | X | X | X | X | X | X | X | X | X | X |
| 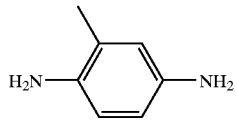 | 2-Methyl-benzene-1,4-diamine | p-Toluene-diamine | X | X | X | X | X | X | X | X | X | | |
|  | Benzene-1,4-diamine | p-Phenylene-diamine | | | | | | | | | | X | X |
| 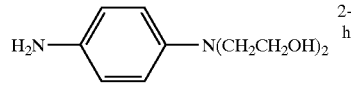 | 2-[(4-Amino-phenyl)-(2-hydroxy-ethyl)-amino]-ethanol | N,N-Bis(2-hydroxyethyl)-p-phenylene-diamine | | | | | | | | | | | |
|  | 4-Amino-phenol | p-Aminophenol | | | | | | | | | | | |
| 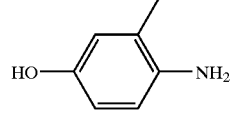 | 4-Amino-3-methyl-phenol | 3-Methyl-p-aminophenol | | | | | | | | | | | |
| 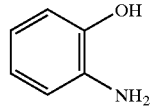 | 2-Amino-phenol | o-Aminophenol | X | | | | | | | | | X | |
| 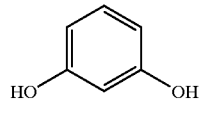 | Benzene-1,3-diol | Resorcinol | | X | | | | | | | | | X |
| 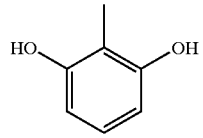 | 2-Methyl-benzene-1,3-diol | 2-Methyl-resorcinol | | | | X | | | | | | | |
| 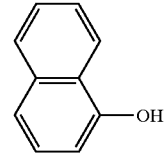 | Naphthalen-1-ol | 1-Naphthol | | | | | X | | | | | | |
| 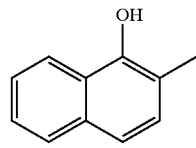 | 2-Methyl-naphthalen-1-ol | 2-Methyl-1-naphthol | | | | | | X | | | | | |

TABLE A-continued

| | Dye Combinations | | | | | | | | | | | | | |
|---|---|---|---|---|---|---|---|---|---|---|---|---|---|---|
| Structure | IUPAC Name | Name | C1 | C2 | C3 | C4 | C5 | C6 | C7 | C8 | C9 | C10 | C11 |
| [structure: 2,4-diaminophenoxyethanol] | 2-(2,4-Diamino-phenoxy)-ethanol | 2,4-Diamino-phenoxyethanol | | | | | | | X | | | | |
| [structure: m-phenylenediamine] | Benzene-1,3-diamine | m-Phenylenediamine | | | | | | | | X | | | |
| [structure: m-aminophenol] | 3-Amino-phenol | m-Aminophenol | | | | | | | | | X | | |
| [structure: 5-amino-2-methylphenol] | 5-Amino-2-methyl-phenol | 2-Hydroxy-4-aminotoluene | | | | | | | | | | X | |
| [structure: 1-hydroxyethyl-4,5-diamino-pyrazole] | 2-(4,5-Diamino-pyrazol-1-yl)-ethanol | 1-Hydroxyethyl-4,5-diamino-pyrazole | | | | | | | | | | | |

TABLE B

| | Dye Combinations | | | | | | | | |
|---|---|---|---|---|---|---|---|---|---|
| Structure | C12 | C13 | C14 | C15 | C16 | C17 | C18 | C19 | C20 |
| [structure with OH, NH-R2, R, NC substituents] | X | X | X | X | X | X | X | X | X |
| [structure: 2-methyl-1,4-diaminobenzene] | | | | | | | | | |
| [structure: p-phenylenediamine] | X | X | X | X | X | X | X | | |
| [structure: N,N-bis(2-hydroxyethyl)-p-phenylenediamine] | | | | | | | | | |
| [structure: p-aminophenol] | | | | | | X | X | | |

TABLE B-continued
Dye Combinations
| Structure | | | | | |
|---|---|---|---|---|---|
| 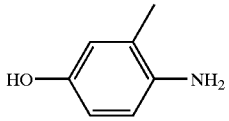 | | | | | |
| 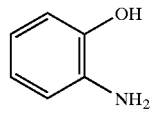 | | | | | X |
| 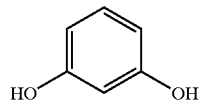 | | | | | X |
| 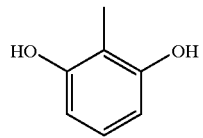 | X | | | | |
| 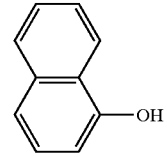 | | X | | | |
| 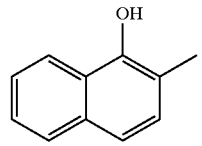 | | | X | | |
| 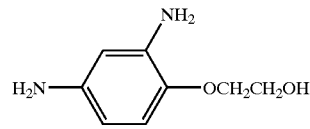 | | | X | | |
| 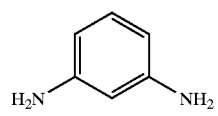 | | | | X | |
| 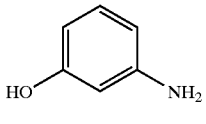 | | | | X | |
| 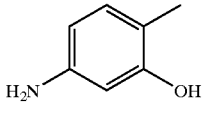 | | | | | X |
| 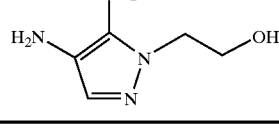 | | | | | |

TABLE B-continued
| | Dye Combinations | | | | | | | | |
|---|---|---|---|---|---|---|---|---|---|
| Structure | C21 | C22 | C23 | C24 | C25 | C26 | C27 | C28 | C29 |
| 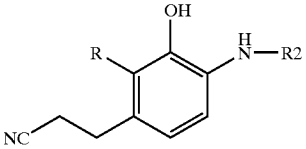 | X | X | X | X | X | X | X | X | X |
| 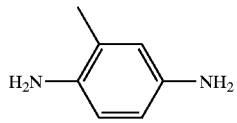 | | | | | | | | | |
| 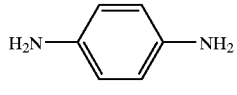 | | | | | | | | | |
| 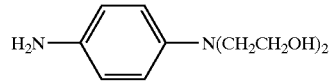 | | | | | | | | | |
|  | X | X | X | X | X | X | X | | |
| 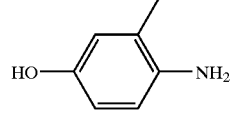 | | | | | | | | X | X |
| 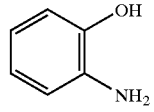 | | | | | | | X | | |
| 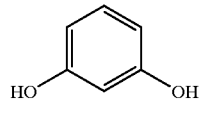 | | | | | | | | | X |
| 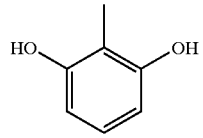 | | X | | | | | | | |
| 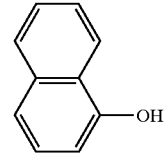 | | | X | | | | | | |
| 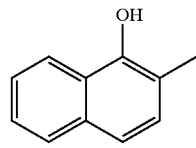 | | | | X | | | | | |

TABLE B-continued
| Dye Combinations | |
|---|---|
| 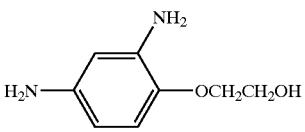 | X |
| H₂N—⌬—NH₂ (m-phenylenediamine) | X |
| HO—⌬—NH₂ (3-amino phenol) | X |
| 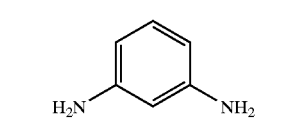 | X |
| 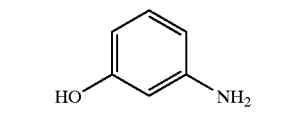 | |
TABLE C
| Structure | C30 | C31 | C32 | C33 | C34 | C35 | C36 | C37 | C38 |
|---|---|---|---|---|---|---|---|---|---|
| 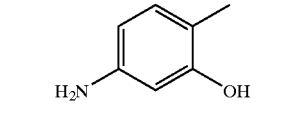 | X | X | X | X | X | X | X | X | X |
| 2-methyl-1,4-phenylenediamine | | | | | | | | | |
| p-phenylenediamine | | | | | | | | | |
| H₂N—⌬—N(CH₂CH₂OH)₂ | | | | | | | X | X | |
| HO—⌬—NH₂ (p-aminophenol) | | | | | | | | | |
| 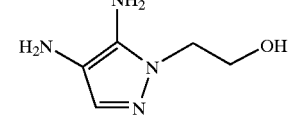 | X | X | X | X | X | X | X | | |

TABLE C-continued

Dye Combinations

| Structure | | | | | | | | | |
|---|---|---|---|---|---|---|---|---|---|
| 2-aminophenol (OH, NH₂) | | | | | | | | X | |
| resorcinol (HO, OH) | | | | | | | | | X |
| 2-methylresorcinol (HO, OH with CH₃) | X | | | | | | | | |
| 1-naphthol | | X | | | | | | | |
| 2-methyl-1-naphthol | | | X | | | | | | |
| 2,4-diamino-1-(2-hydroxyethoxy)benzene | | | | X | | | | | |
| m-phenylenediamine (H₂N, NH₂) | | | | | X | | | | |
| 3-aminophenol (HO, NH₂) | | | | | | X | | | |
| 5-amino-2-methylphenol (H₂N, OH) | | | | | | | X | | |
| 4,5-diamino-1-(2-hydroxyethyl)pyrazole | | | | | | | | | |

| Structure | C39 | C40 | C41 | C42 | C43 | C44 | C45 | C46 | C47 |
|---|---|---|---|---|---|---|---|---|---|
| [Structure with OH, R, NH—R2, and NC substituents on benzene ring] | X | X | X | X | X | X | X | X | X |

TABLE C-continued

Dye Combinations

| Structure | | | | | | | | | |
|---|---|---|---|---|---|---|---|---|---|
| 2-methyl-1,4-diaminobenzene | | | | | | | | X | X |
| 1,4-diaminobenzene | | | | | | | | | |
| 4-amino-N,N-bis(2-hydroxyethyl)aniline | X | X | X | X | X | X | X | | |
| 4-aminophenol | | | | | | | | | |
| 4-amino-3-methylphenol | | | | | | | | | |
| 2-aminophenol | | | | | | | | X | |
| resorcinol | | | | | | | | X | X |
| 2-methylresorcinol | | X | | | | | | | X |
| 1-naphthol | | | | X | | | | | |
| 2-methyl-1-naphthol | | | | | | X | | | |
| 2,4-diamino-1-(2-hydroxyethoxy)benzene | | | | | | X | | | |
| 1,3-diaminobenzene | | | | | | | X | | |

TABLE C-continued

Dye Combinations

| Structure | |
|---|---|
| 3-aminophenol (HO-C6H4-NH2) | X |
| 5-amino-2-methylphenol (H2N-C6H3(CH3)-OH) | X |
| 4,5-diamino-1-(2-hydroxyethyl)pyrazole | |

TABLE D

Dye Combinations

| Structure | C48 | C49 | C50 | C51 | C52 | C53 | C54 | C55 | C56 |
|---|---|---|---|---|---|---|---|---|---|
| substituted phenol with R, NHR2, CN-CH2CH2- groups | X | X | X | X | X | X | X | X | X |
| 2-methyl-1,4-phenylenediamine | X | X | X | X | X | X | | | |
| 1,4-phenylenediamine | | | | | | | X | X | X |
| N,N-bis(2-hydroxyethyl)-p-phenylenediamine | | | | | | | | | |
| 4-aminophenol | | | | | | | | | |
| 4-amino-3-methylphenol | | | | | | | | | |
| 2-aminophenol | | | | | | | X | | |
| resorcinol | X | X | X | X | X | X | X | X | X |

TABLE D-continued

| Dye Combinations | | | | | | | | | |
|---|---|---|---|---|---|---|---|---|---|
| 2-methylresorcinol (HO-C6H3(CH3)-OH) | | | | | | | | X | |
| 1-naphthol | X | | | | | | | | X |
| 2-methyl-1-naphthol | | X | | | | | | | |
| 2-amino-4-(2-hydroxyethoxy)aniline | | X | | | | | | | |
| m-phenylenediamine | | | X | | | | | | |
| 3-aminophenol | | | | | | X | | | |
| 5-amino-2-methylphenol | | | | | | | X | | |
| 4,5-diamino-1-(2-hydroxyethyl)pyrazole | | | | | | | | | |

| Structure | C57 | C58 | C59 | C60 | C61 | C62 | C63 | C64 | C65 |
|---|---|---|---|---|---|---|---|---|---|
| (OH / R / NH-R2 / NC substituted benzene) | X | X | X | X | X | X | X | X | X |
| 2-methyl-p-phenylenediamine | | | | | | | | | |
| p-phenylenediamine | X | X | X | X | X | | | | |

TABLE D-continued

Dye Combinations

| Structure | | | | | | | | | | | | | |
|---|---|---|---|---|---|---|---|---|---|---|---|---|---|
| $H_2N$-C₆H₄-$N(CH_2CH_2OH)_2$ | | | | | | | | | | | | | |
| HO-C₆H₄-$NH_2$ | | | | | | | X | X | X | X | | | |
| HO-C₆H₃(CH_3)-$NH_2$ | | | | | | | | | | | | | |
| 2-aminophenol (OH, $NH_2$) | | | | | | X | | | | | | | |
| resorcinol (HO-C₆H₄-OH) | X | X | X | X | X | X | X | X | X | | | | |
| 2-methylresorcinol | | | | | | | | X | | | | | |
| 1-naphthol | | | | | | | | | X | | | | |
| 2-methyl-1-naphthol | X | | | | | | | | | X | | | |
| 2,4-diamino-1-(2-hydroxyethoxy)benzene | X | | | | | | | | | | | | |
| m-phenylenediamine | | | X | | | | | | | | | | |
| m-aminophenol (HO, $NH_2$) | | | | X | | | | | | | | | |
| 5-amino-2-methylphenol | | | | | X | | | | | | | | |

TABLE D-continued
Dye Combinations
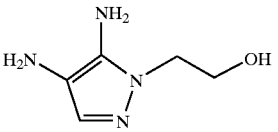
TABLE E
Dye Combinations
| Structure | C66 | C67 | C68 | C69 | C70 | C71 | C72 | C73 | C74 |
|---|---|---|---|---|---|---|---|---|---|
| 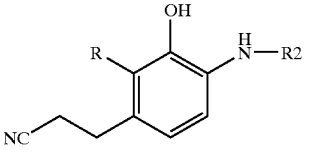 | X | X | X | X | X | X | X | X | X |
| 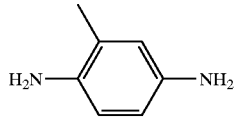 | | | | | | | | | |
| 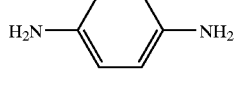 | | | | | | | | | |
| 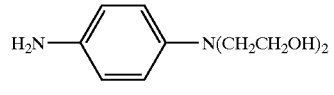 | | | | | | | | | |
| 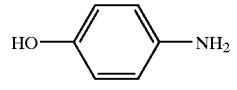 | X | X | X | X | | | | | |
| 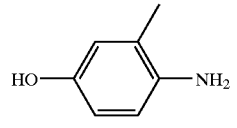 | | | | | X | X | X | X | X |
| 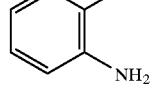 | | | | | X | | | | |
| 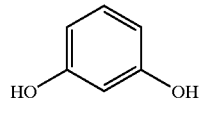 | X | X | X | X | X | X | X | X | X |
| 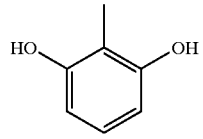 | | | | | | X | | | |

TABLE E-continued

Dye Combinations

| Structure | | | | | | | | | X |
|---|---|---|---|---|---|---|---|---|---|
| 1-naphthol | | | | | | | | | |
| 2-methyl-1-naphthol | | | | | | | | X | |
| 2,4-diamino-phenoxyethanol | X | | | | | | | | X |
| m-phenylenediamine (1,3-diaminobenzene) | | X | | | | | | | |
| 3-aminophenol | | | | X | | | | | |
| 5-amino-2-methylphenol | | | | | X | | | | |
| 4,5-diamino-1-(2-hydroxyethyl)pyrazole | | | | | | | | | |

| Structure | C75 | C76 | C77 | C78 | C79 | C80 | C81 | C82 | C83 |
|---|---|---|---|---|---|---|---|---|---|
| cyanophenol derivative (R, R2 substituted) | X | X | X | X | X | X | X | X | X |
| 2-methyl-1,4-diaminobenzene | | | | | | | | | |
| 1,4-diaminobenzene | | | | | | | | | |
| N,N-bis(2-hydroxyethyl)-p-phenylenediamine | | | | | | | | | |

TABLE E-continued
Dye Combinations
| Structure | | | | | | | |
|---|---|---|---|---|---|---|---|
|  4-aminophenol | | | | | | | |
| 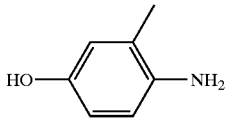 | X | X | X | | | | |
| 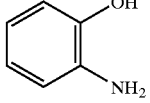 | | | | X | | | |
| 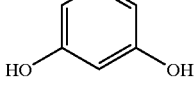 resorcinol | X | X | X | | X | | |
| 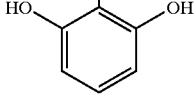 | | | | | | X | |
| 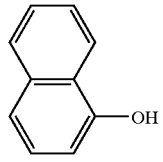 1-naphthol | | | | | | X | |
| 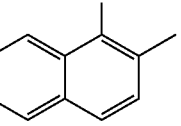 | | | | | | | X |
|  | | | | | | | X |
| 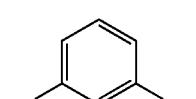 m-phenylenediamine | | X | | | | | |
| 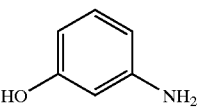 | | | X | | | | |
| 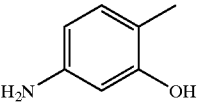 | | | X | | | | |

TABLE E-continued
Dye Combinations
| Structure | | | | | | |
|---|---|---|---|---|---|---|
| 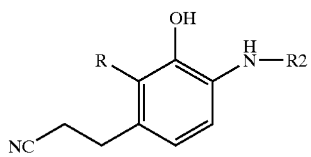 | X | X | X | X | X | X |
TABLE F
Dye Combinations
| Structure | C84 | C85 | C86 | C87 | C88 | C89 | C90 | C91 | C92 |
|---|---|---|---|---|---|---|---|---|---|
| OH, R, NH—R2, NC (phenyl) | X | X | X | X | X | X | X | X | X |
| 2-methyl-1,4-phenylenediamine | | | | | | | | | |
| 1,4-phenylenediamine | | | | | | | | | |
| $H_2N$-C$_6$H$_4$-N(CH$_2$CH$_2$OH)$_2$ | | | | | | | | | |
| 4-aminophenol | | | | | | | | | |
| 2-methyl-4-aminophenol | | | | | | | | | |
| 2-aminophenol | | | | X | | | | | |
| resorcinol | | | | X | X | X | X | X | X |
| 2-methylresorcinol | | | | | X | | | | |

TABLE F-continued

Dye Combinations

| Structure | | | | | | | | | |
|---|---|---|---|---|---|---|---|---|---|
| 1-naphthol (naphthalen-1-ol) | | | | | | | X | | |
| 2-methyl-naphthalen-1-ol | | | | | | | | X | |
| 2,4-diamino-1-(2-hydroxyethoxy)benzene | | | | | | | | X | |
| m-phenylenediamine (benzene-1,3-diamine) | X | | | | | | | | X |
| 3-aminophenol | | X | | | | | | | |
| 5-amino-2-methylphenol | | | X | | | | | | |
| 4,5-diamino-1-(2-hydroxyethyl)pyrazole | X | X | X | X | X | X | X | X | X |

| Structure | C93 | C94 | C95 | C96 | C97 | C98 | C99 | C100 | C101 |
|---|---|---|---|---|---|---|---|---|---|
| 3-(cyanoethyl)-2-R-6-(R2-amino)phenol | X | X | X | X | X | X | X | X | X |
| 2-methyl-benzene-1,4-diamine | | | | | | | | | |
| benzene-1,4-diamine (p-phenylenediamine) | | | | | | | | | |
| N,N-bis(2-hydroxyethyl)-p-phenylenediamine | | | | | | | | | |

TABLE F-continued

Dye Combinations

| Structure | | | | | | | | | | |
|---|---|---|---|---|---|---|---|---|---|---|
| 4-aminophenol (HO-C6H4-NH2) | | | | | | | | | | |
| 4-amino-3-methylphenol | | | | | | | | | | |
| 2-aminophenol | | X | | | | | | | | |
| resorcinol (1,3-dihydroxybenzene) | X | X | | X | | | | | | |
| 2-methylresorcinol | | | | | X | | | | | |
| 1-naphthol | | | | | X | | | | | |
| 2-methyl-1-naphthol | | | | | | X | | | | |
| 2,4-diamino-1-(2-hydroxyethoxy)benzene | | | | | | | X | | | |
| 1,3-diaminobenzene | | | | | | | | | X | |
| 3-aminophenol | | X | | X | X | X | X | X | X | X |
| 5-amino-2-methylphenol | X | | | | | | | | | |

TABLE F-continued
| Dye Combinations |
|---|
| 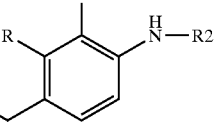 | X X X X X X X X X |
TABLE G
| | Dye Combinations | | | | | | | | |
|---|---|---|---|---|---|---|---|---|---|
| Structure | C102 | C103 | C104 | C105 | C106 | C107 | C108 | C109 | C110 |
| 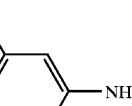 | X | X | X | X | X | X | X | X | X |
| 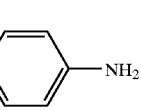 | | X | X | X | X | X | X | X | X |
| 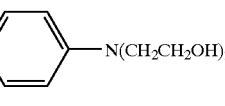 | | | | | | | | | |
| 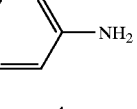 | | | | | | | | | |
| 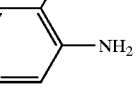 | | X | X | X | X | X | X | X | X |
| 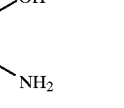 | | | | | | | | | |
| 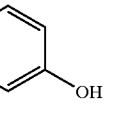 | | | X | | | | | | |
| 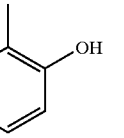 | | | | X | | | | | |
|  | | | | | X | | | | |

TABLE G-continued

Dye Combinations

| Structure | | | | | | | | | |
|---|---|---|---|---|---|---|---|---|---|
| 1-naphthol | | | | X | | | | | |
| 1-hydroxy-2-methylnaphthalene | | | | | X | | | | |
| 2,4-diamino-1-(2-hydroxyethoxy)benzene | | | | | X | | | | |
| m-phenylenediamine | | | | | | X | | | |
| 3-aminophenol | X | | | | | | | | X |
| 5-amino-2-methylphenol | X | | | | | | | | |
| 4,5-diamino-1-(2-hydroxyethyl)pyrazole | X | | | | | | | | |

| Structure | C111 | C112 | C113 | C114 | C115 | C116 | C117 | C118 | C119 |
|---|---|---|---|---|---|---|---|---|---|
| (OH, NH-R2, R, CN substituted benzene) | X | X | X | X | X | X | X | X | X |
| 2-methyl-1,4-phenylenediamine | X | | | | | | | | |
| 1,4-phenylenediamine | | X | X | X | X | X | X | X | X |
| N,N-bis(2-hydroxyethyl)-p-phenylenediamine | | | | | | | | | |

TABLE G-continued

Dye Combinations

| Structure | 1 | 2 | 3 | 4 | 5 | 6 | 7 | 8 | 9 |
|---|---|---|---|---|---|---|---|---|---|
| HO—C6H4—NH2 (4-aminophenol) | X | X | X | X | X | X | X | X | X |
| HO—C6H3(CH3)—NH2 (methyl aminophenol) | | | | | | | | | |
| 2-aminophenol | | | X | | | | | | |
| resorcinol (1,3-dihydroxybenzene) | | | | X | | | | | |
| 2-methylresorcinol | | | | | X | | | | |
| 1-naphthol | | | | | | X | | | |
| 2-methyl-1-naphthol | | | | | | | X | | |
| 2,4-diamino-1-(2-hydroxyethoxy)benzene | | | | | | | | X | |
| m-phenylenediamine | | | | | | | | X | |
| m-aminophenol | | | | | | | | | X |
| 4-amino-2-methylphenol (4-amino-o-cresol) | | | X | | | | | | |

TABLE G-continued
Dye Combinations
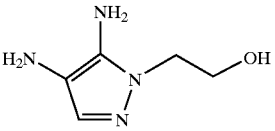
TABLE H
Dye Combinations
| Structure | C120 | C121 | C122 | C123 | C124 | C125 | C126 | C127 | C128 | C129 |
|---|---|---|---|---|---|---|---|---|---|---|
| 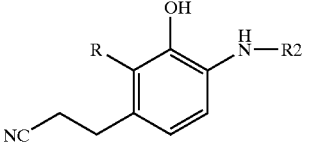 | X | X | X | X | X | X | X | X | X | X |
| 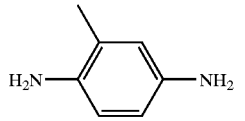 |  | X | X | X | X | X | X | X | X | X |
|  | X |  |  |  |  |  |  |  |  |  |
| 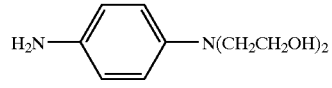 |  |  |  |  |  |  |  |  |  |  |
| 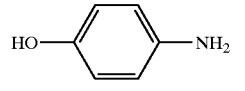 | X |  |  |  |  |  |  |  |  |  |
| 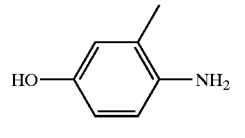 |  |  | X | X | X | X | X | X | X | X |
| 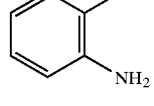 |  | X |  |  |  |  |  | X |  |  |
| 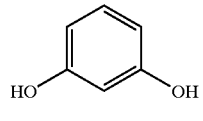 |  | X |  |  |  |  |  |  |  | X |
| 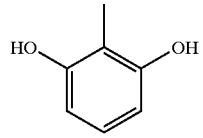 |  |  |  | X |  |  |  |  |  |  |

TABLE H-continued

Dye Combinations

| Structure | | | | | | | | | |
|---|---|---|---|---|---|---|---|---|---|
| 1-naphthol | | | | X | | | | | |
| 2-methyl-1-naphthol | | | X | | | | | | |
| 2,4-diamino-1-(2-hydroxyethoxy)benzene | | | X | | | | | | |
| m-phenylenediamine | | | | | X | | | | |
| 3-aminophenol | | | | | | X | | | |
| 5-amino-2-methylphenol | X | | | | | | | X | |
| 4,5-diamino-1-(2-hydroxyethyl)pyrazole | | | | | | | | | |

| Structure | C130 | C131 | C132 | C133 | C134 | C135 | C136 | C137 | C138 |
|---|---|---|---|---|---|---|---|---|---|
| 2-OH-3-R-4-(R2NH)-phenyl cyanomethyl | X | X | X | X | X | X | X | X | X |
| 2-methyl-1,4-phenylenediamine | | | | | | | | | |
| 1,4-phenylenediamine | X | X | X | X | X | X | X | X | X |
| N,N-bis(2-hydroxyethyl)-1,4-phenylenediamine | | | | | | | | | |

TABLE H-continued
Dye Combinations
| Structure | | | | | | | | | | | |
|---|---|---|---|---|---|---|---|---|---|---|---|
|  HO—⟨⟩—NH₂ | | | | | | | | | | | |
| 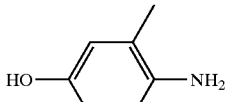 2-methyl-4-aminophenol | X | X | X | X | X | X | X | X | X | | |
| 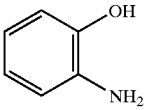 2-aminophenol | | | | | | | | | | | |
| 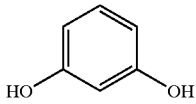 resorcinol | | | | | | | | | | | |
| 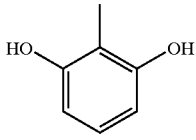 2-methylresorcinol | X | | | | | | | | | | |
| 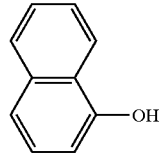 1-naphthol | | X | | | | | | | | | |
| 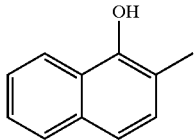 2-methyl-1-naphthol | | | X | | | | | | | | |
| 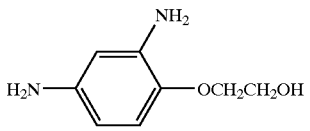 2,4-diamino-1-(β-hydroxyethoxy)benzene | | | | X | | | | | | | |
| 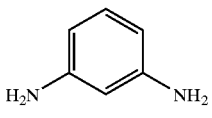 m-phenylenediamine | | | | | X | | | | | | |
| 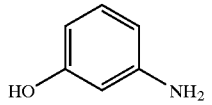 3-aminophenol | | | | | | X | | | | | |

TABLE H-continued

Dye Combinations

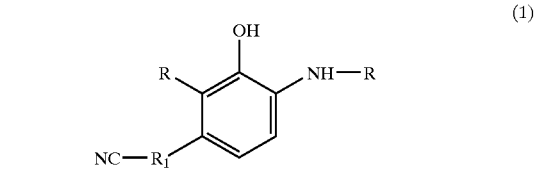

X

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A hair dyeing composition at least a compound of formula I and a developer Formula (1):

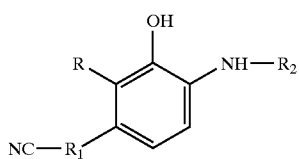
(1)

wherein R is a moiety selected from the group consisting of H, $C_{1-3}$ alkyl and $C_{1-3}$ hydroxyalkyl; $R_1$ is a $C_{1-3}$ alkylene radical and $R_2$ is selected from the group consisting of H and $C_{1-3}$ alkyl radicals.

2. The hair dyeing composition according to claim 1 wherein R is H, $R_1$ is ethylene and $R_2$ is H.

3. A process for dyeing hair wherein at least one compound is coupled in the presence of an oxidizing agent to produce an oxidative hair dye, wherein the at least one compound comprises a compound of the Formula (1):

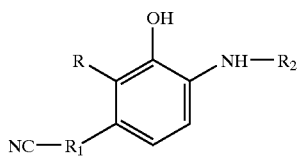
(1)

wherein R is a moiety selected from the group consisting of H, $C_{1-3}$ alkyl and $C_{1-3}$ hydroxyalkyl; $R_1$ is a $C_{1-3}$ alkylene radical and $R_2$ is selected from the group consisting of H and $C_{1-3}$ alkyl radicals.

4. The process for dyeing hair according to claim 3 wherein R is H, $R_1$ is ethylene and $R_2$ is H.

5. A hair dyeing composition comprising, in a suitable carrier, effective amount of:
(a) at least one compound that couples in the presence of an oxidizing agent; and
(b) at least one oxidizing agent;
wherein at least one compound comprises a coupler of Formula (1):

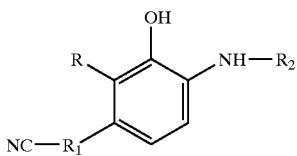
(1)

wherein R is a moiety selected from the group consisting of H, $C_{1-3}$ alkyl and $C_{1-3}$ hydroxyalkyl; $R_1$ is a $C_{1-3}$ alkylene radical and $R_2$ is selected from the group consisting of H and $C_{1-3}$ alkyl radicals.

6. The hair dyeing composition according to claim 5 wherein R is H, $R_1$ is ethylene and $R_2$ is H.

7. A hair dyeing composition comprising, in a suitable carrier, an effective amount of:
(a) at least one compound of Formula (1):

(1)

wherein R is a moiety selected the group consisting of from H, $C_{1-3}$ alkyl and $C_{1-3}$ hydroxyalkyl; $R_1$ is a $C_{1-3}$ alkylene radical and $R_2$ is selected from the group consisting of H and $C_{1-3}$ alkyl radicals, and
(b) at least one other coupler and optionally at least one primary intermediate, and
(c) at least one oxidizing agent.

8. The hair dyeing composition according to claim 7 wherein R is H, $R_1$ is ethylene and $R_2$ is H.

9. A process for dyeing hair comprising applying an effective amount of a hair dyeing composition of claim 5 to the hair; permitting the composition to contact the hair for a period of time effective to dye the hair, and then rinsing the hair dyeing composition from the hair.

10. A process for dyeing hair comprising applying an effective amount of a hair dyeing composition of claim 6 to the hair; permitting the composition to contact the hair for a period of time effective to dye the hair, and then rinsing the hair dyeing composition from the hair.

11. A process for dyeing hair comprising applying an effective amount of a hair dyeing composition of claim 7 to the hair; permitting the composition to contact the hair for a period of time effective to dye the hair, and then rinsing the hair dyeing composition from the hair.

12. A process for dyeing hair comprising applying an effective amount of a hair dyeing composition of claim 8 to the hair; permitting the composition to contact the hair for a period of time effective to dye the hair, and then rinsing the hair dyeing composition from the hair.

13. A compound of Formula (1):

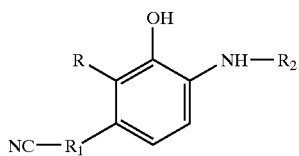
(1)

wherein R is a moiety selected from he group consisting of H, $C_{1-3}$ alkyl and $C_{1-3}$ hydroxyalkyl; $R_1$ is a $C_{1-3}$ alkylene radical and $R_2$ is selected from the group consisting of H and $C_{1-3}$ alkyl radicals.

14. A compound according to claim 13 wherein R is H, $R_1$ is ethylene and $R_2$ is H.

15. A hair dye composition comprising, in a suitable carrier, an effective amount of at least one compound of Formula (1):

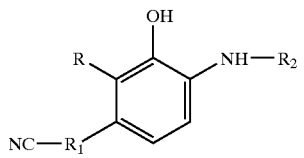
(1)

wherein R is a moiety selected from he group consisting of H, $C_{1-3}$ alkyl and $C_{1-3}$ hydroxyalkyl; $R_1$ is a $C_{1-3}$ alkylene radical and $R_2$ is selected from the group consisting of H and $C_{1-3}$ alkyl radicals.

16. The hair dye composition of claim 15 wherein R is H, $R_1$ is ethylene and $R_2$ is H.

17. The hair dye composition of claim 15 further comprising at least one oxidation dye other than the compound of Formula (1).

18. The hair dye composition of claim 17 wherein said at least one oxidation dye is a coupler.

19. The hair dye composition of claim 18 further containing a primary intermediate other than at least one oxidation dye.

* * * * *

UNITED STATES PATENT AND TRADEMARK OFFICE
CERTIFICATE OF CORRECTION

PATENT NO. : 6,835,213 B2
DATED : December 28, 2004
INVENTOR(S) : Mu-Ill et al.

It is certified that error appears in the above-identified patent and that said Letters Patent is hereby corrected as shown below:

Column 60,
Line 20, delete the chemical structure and replace it with:

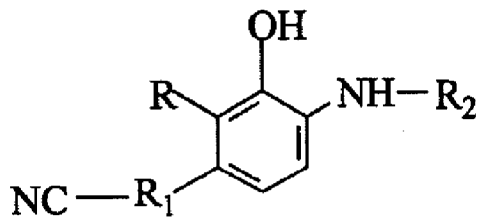

(1)

Signed and Sealed this

Twenty-fourth Day of May, 2005

JON W. DUDAS
*Director of the United States Patent and Trademark Office*